United States Patent [19]

Hahn

[11] Patent Number: 4,468,401
[45] Date of Patent: Aug. 28, 1984

[54] METHOD OF BLOCKING PERIPHERAL NOREPINEPHRINE RELEASE

[75] Inventor: Richard A. Hahn, Indianapolis, Ind.

[73] Assignee: Eli Lilly and Company, Indianapolis, Ind.

[21] Appl. No.: 438,833

[22] Filed: Nov. 3, 1982

[51] Int. Cl.$^3$ .................... A61K 31/47; C07D 471/04
[52] U.S. Cl. ...................................... 424/258; 546/82
[58] Field of Search .......................... 424/258; 546/82

[56] References Cited

U.S. PATENT DOCUMENTS 4,198,415  4/1980  Kornfeld et al. ................... 546/165
4,298,611  11/1981  Fernstrom et al. ................ 424/261

OTHER PUBLICATIONS

Bach et al., Chem. Abs. 92:215331u.
Buylaert et al., *Vasodilatation*, 125 (Ed. Vanhoutte and Leusen, Raven Press, New York, 1981).
Kolloch et al., *Hypotension*, 2, 390 (1980).
Lefevre-Borg et al., *Clinical Science*, 59, 291s–294s (1980).
Cavero et al., Abstract Submitted to the International Society of Hypertension, Spring 1981 Meeting.
Lokhandwala et al., *J. Pharm. Exper. Therap.*, 211, 620 (1979).
Clark et al., *Acta Endocrin.*, 88, 75 (1978).
Nilsson et al., *Acta Endocrin.*, 88, 83 (1978).
Greenacre et al., *Br. J. Clin. Pharmac.*, 3, 571 (1976).
Stumpe et al., *Lancet*, 211 (Jul. 30, 1977).
Hahn and Farrell, *Life Sciences*, 28, 2497 (1981).
Hahn, *Life Sciences*, 29, 2501 (1981).
Yen et al., *Life Sciences*, 25, 209 (1979).
Lokhandwala and Barrett, *J. Auton. Pharmac.*, 3, 189 (1982).
Tsuruta et al., *Nature*, 292, 463 (1981).
Rabey et al., *Brain Research*, 225, 347 (1981).
Rabey et al., Paper Presented at Fall Meeting of the American Society for Pharmacology and Experimental Therapeutics, Aug. 1980, Abstract 427.
Goldstein and Kinugasa, *The Pharmacologist*, 24, 137 (1982).
Hahn et al., *J. Pharm. Exper. Therap.*, 224, 206 (1983).

*Primary Examiner*—Jane T. Fan
*Attorney, Agent, or Firm*—James L. Rowe; Arthur R. Whale

[57] ABSTRACT

Trans-4aR-5-n-propyl-4,4a,5,6,7,8,8a,9-octahydro-1H(and 2H)pyrazolo[3,4-g]quinoline and pharamceutically-acceptable salts thereof, blocks norepinephrine release from peripheral sympathetic nerve terminals that innervate arterial muscle fibers in hypertensive mammals to reduce blood pressure.

4 Claims, No Drawings

METHOD OF BLOCKING PERIPHERAL NOREPINEPHRINE RELEASE

This invention provides a novel method of blocking norepinephrine release from peripheral sympathetic nerve terminals that innervate arterial muscle fibers in mammals which comprises administering to a mammal having an elevated blood pressure an effective dose of a tautomeric mixture of trans-4aR-5-n-propyl-4,4a,5,6,7,8,8a,9-octahydro-2H-pyrazolo[3,4-g]quinoline (Ia) and trans-4aR-5-n-propyl-4,4a,5,6,7,8,8a,9-octahydro-1H-pyrazolo[3,4-g]quinoline (Ib) represented by the formulas:

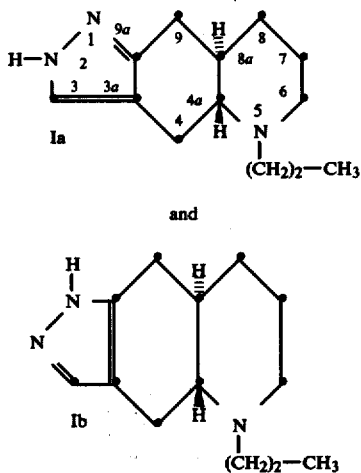

or a pharmaceutically-acceptable acid addition salt thereof, formed with a non-toxic acid, thereby lowering the blood pressure of said mammal.

Alternate and equally acceptable chemical names for the racemic pair Ia and Ib above include 5-n-propyl-4,4aβ,5,6,7,8,8aα,9-octahydro-2H(and 1H)-pyrazolo[3,4-g]quinoline, 4aR,8aR-4,4a,5,6,7,8,8a,9-octahydro-2H(and 1H)pyrazoloquinoline, trans-l-5-n-propyl-4,4a,5,6,7,8,8a,9-octahydro-2H(and 1H)pyrazolo[3,4-g]quinoline and trans-4aR-4,4a,5,6,7,8,8a,9-octahydro-2H(and 1H)pyrazolo[3,4-g]quinoline, the latter name being preferred.

Of the tautomers shown above, it is believed that, in most ordinary chemical environments, tautomer Ia—the 2H tautomer—predominates.

Compounds according to the above structure contain two basic groups, the alkylated quinoline ring nitrogen and the pyrazole nitrogen carrying the hydrogen (N-1 or N-2). The quinoline ring nitrogen is the more basic of the two and forms acid addition salts readily. Strong inorganic acids such as the mineral acids or strong organic acids such as p-toluenesulfonic acid, can form di salts when employed in excess.

Pharmaceutically-acceptable acid addition salts of the compounds of this invention thus include mono or di salts derived from inorganic acids such as: hydrochloric acid, nitric acid, phosphoric acid, sulfuric acid, hydrobromic acid, hydriodic acid, phosphorous acid and the like, as well as salts derived from organic acids such as aliphatic mono and dicarboxylic acids, phenyl-substituted alkanoic acids, hydroxy alkanoic and alkandioic acids, aromatic acids, aliphatic and aromatic sulfonic acids, etc. Such pharmaceutically-acceptable salts thus include sulfate, pyrosulfate, bisulfate, sulfite, bisulfite, nitrate, phosphate, monohydrogen-phosphate, dihydrogenphosphate, metaphosphate, pyrophosphate, chloride, bromide, iodide, fluoride, acetate, propionate, decanoate, caprylate, acrylate, formate, isobutyrate, caprate, heptanoate, propiolate, oxalate, malonate, succinate, suberate, sebacate, fumarate, maleate, mandelate, butyne-1,4-dioate, hexyne-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, β-hydroxybutyrate, glycollate, malate, tartrate, methanesulfonate, propanesulfonate, naphthalene-1-sulfonate, naphthalene-2-sulfonate and the like salts.

Tautomers represented by Ia and Ib above can be prepared by resolving the racemic tautomeric mixture, trans-dl-5-n-propyl-4,4a,5,6,7,8,8a,9-octahydro-2H(and 1H)pyrazolo[3,4-g]quinoline, provided by U.S. Pat. No. 4,198,415. Such a resolution is described in the copending application of Titus et al. Ser. No. 439,238, filed this even day herewith. According to this procedure, the racemic mixture is treated with S-2,3-dihydroxybutanedioic acid or D-(−)-S-tartaric acid. The D-(−)-S-tartrate salt of trans-4aR-5-n-propyl-4,4a,5,6,7,8,8a,9-octahydro-2H(and 1H)-pyrazole[3,4-g]quinoline is isolated and purified. Alternatively, the process of Schaus and Booher, described in copending application Ser. No. 439,107 filed this even day herewith, can be employed wherein an intermediate ketone, trans-dl-1-n-propyl-6-oxodecahydroquinoline, also named as trans-(±)-1-n-propyl-6-oxodecahydroquinoline, is resolved into its component diastereoisomers. One of these diastereoisomers, trans-8aR-1-n-propyl-6-oxodecahydroquinoline,

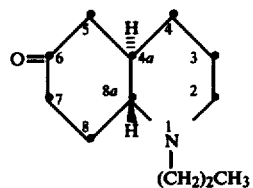

can be transformed into Ia and Ib by either the procedure set forth in Schaus Ser. No. 438,834 filed this even date or by the procedure set forth in U.S. Pat. No. 4,198,415.

Both the above processes yield a salt, [D-(−)-S-tartrate or diHCl]. Conversion of the salt to the free base is readily effected by dissolving the salt in water and then adding an excess of a base (NaOH, Na₂CO₃ etc.). The pyrazolo [3,4-g]quinoline, being insoluble in the basic solution, separates and is extracted with a water-immiscible organic solvent. The organic layer is separated and dried. If it is desired to prepare a different salt, a solution containing one equivalent of a second non-toxic acid can then be added, and the salt isolated by filtration or evaporation. Alternatively, the solvent can be removed from the dried organic extract and the free base obtained as a residue. The free base can then be dissolved in a suitable solvent and the different non-toxic acid added as a solution. The preferred salt for use in the novel processes and formulations if this invention is the mono HCl salt and can be prepared for example by adding an equivalent of ethanolic hydrogen chloride to an ethanol solution of the free base, followed by evaporation of the ethanol and recrystallization of the salt. If it is desired to make a disalt such as a dihydrochloride salt, HCl gas can be passed into a solution of the free base to the point of saturation and the salt isolated by filtration.

In carrying out my novel therapeutic process, a pharmaceutically-acceptable salt of a drug according to Ia and Ib above formed with a non-toxic acid is administered orally or parenterally to a mammal with an elevated blood pressure in which it is desirable to lower blood pressure, by blocking norepinephrine release from peripheral sympathetic nerve terminals that innervate arterial muscle fibers. For parenteral administration, a water soluble salt of the drug, trans-4aR-5-n-propyl-4,4a,5,6,7,8,8a,9-octahydro-2H(and 1H)-pyrazolo[3,4-g]isoquinoline, is dissolved in an isotonic salt solution and administered by the iv route. Dose levels of from 0.5-500 mcg./kg. of mammalian weight are found to be effective to block norepinephrine release and thereby reduce elevated blood pressure in spontaneously hypertensive rats (SHR). For oral administration, a pharmaceutically-acceptable salt of the drug is mixed with standard pharmaceutical excipients such as starch and loaded into capsules, each containing 0.1-15 mg. of active drug. Dosage levels of from 0.1-3 mg./kg. have been found to be effective in blocking norepinephrine release from sympathetic nerve terminals, thereby lowering blood pressure in SHR, for periods ranging up to six hours. Thus, the oral dosage would be administered 3-4 times per day, giving a daily dosage range of about 0.1 to about 15 mg./kg. per day.

Other oral dosage forms, suspension, elixers and tablets, can also be utilized and are preparable by standard procedures.

The effect of the method of this invention in blocking norepinephrine release from peripheral sympathetic nerve terminals that innervate arterial muscle fibers, thereby reducing the blood pressure in spontaneously hypertensive rats, is illuminated by the following experiment:

Adult male spontaneously hypertensive rats (SHR) (Taconic Farms, Germantown, N.Y.), weighing approximately 300 g. were anesthetized with pentobarbital sodium (60 mg./kg., i.p.). The trachea was cannulated and SHR respired room air. Pulsatile arterial blood pressure was measured from a cannulated carotid artery using a Statham transducer (P23 ID). Mean arterial blood pressure was calculated as diastolic blood pressure plus ⅓ pulse pressure. Cardiac rate was monitored by a cardiotachometer which was triggered by the systolic pressure pulse. Drug solutions were administered i.v. through a catheter placed in a femoral vein. Arterial blood pressure and cardiac rate were recorded on a multichannel oscillograph (Beckman, Model R511A). Fifteen minutes were allowed to elapse following surgery for equilibration of the preparation.

Table I which follows gives the results of this experiment, using trans-4aR-5-n-propyl-4,4a,5,6,7,8,8a,9-octahydro-2H(and 1H)pyrazolo[3,4-g]quinoline D-(−)-S-tartrate, plus the corresponding trans-4aS-enantiomer and the parent trans-dl-racemate as the hydrochloride salt for comparison purposes. Each drug was administered i.v. to groups of four SHR at a series of dose levels.

TABLE 1

Relative potencies of trans-5-n-propyl-4,-4a,5,6,7,8,8a,9-octahydro-2H(and 1H)pyrazolo[3,4-g]-quinolines isomers and racemate.

| Compound | Dose mcg./kg. | Mean Arterial Blood Pressure % Change (±) |
|---|---|---|
| Trans-4aR | 0.1 | −7.7 ± 1.6 |
|  | 1 | −14.3 ± 1.6 |
|  | 10 | −25.2 ± 2.1 |
|  | 100 | −38.6 ± 4.3 |
| Trans-4aS | 0.1 | −8.5 ± 0.8 |
|  | 1 | −5.1 ± 0.8 |
|  | 10 | −5.0 ± 0.3 |
|  | 100 | −4.6 ± 0.3 |
|  | 1000 | −6.4 ± 1.1 |
| Trans-dl | 1 | −12.7 ± 2.2 |
|  | 10 | −22.4 ± 0.7 |
|  | 100 | −32.0 ± 2.1 |
|  | 1000 | −52.2 ± 6.9 |

It is apparent that all the hypotensive action of trans-dl-5-n-propyl-4,4a,5,6,7,8,8a,9-octahydro-1H(and 2H)-pyrazolo[3,4-g]quinoline resides in the levo or trans-4aR stereoisomer.

More direct evidence that trans-dl-5-n-propyl-4,4a,5,6,7,8,8a,9-octahydro-1H-(and 2H)-pyrazolo[3,4-g]quinoline blocks norepinephrine release from peripheral sympathetic nerve terminals is illustrated by the following experiment. In this experiment, SHR were pithed by passing a steel rod through the right orbit and down the entire length of the spinal column. The rod was left in position for the duration of the experiment. Immediately after pithing, SHR were ventilated with room air delivered from a rodent respirator (Harvard, Model 680; tidal volume of 1 ml./100 g. body weight, 60 cycles/min). The pitching rod was used to stimulate the entire sympathetic outflow from the spinal cord. Portions of the rod which lay in the cervical and sacral cord were insulated. The sympathetic outflow was stimulated by square wave pulses (50 volts, 1 msec duration for 30 sec) of frequencies of 0.25, 1, 4 and 8 Hz delivered from a stimulator (Grass, Model S44). The pithing rod served as the stimulating electrode while a needle inserted into the right hindlimb musculature was the indifferent electrode. Skeletal muscle twitches were prevented by administration of d-tubocurarine (1 mg./kg., i.v.). Increments in diastolic blood pressure produced by electrical stimulation of the sympathetic outflow were monitored from a cannulated carotid artery. The test drug was administered i.v. at two dose levels to groups of four SHR.

Table 2 which follows indicates that electrical stimulation of the sympathetic outflow or i.v. administration of exogenous norepinephrine each produced the expected vasoconstrictor responses in control pithed SHR, as indicated by the increments in diastolic blood pressure. Pretreatment of other SHR with the trans-dl-racemate attenuated neurogenic vasoconstrictor responses in a dose-related manner. This attenuation was selective in that the test drug produced no concomitant antagonism of comparable vasoconstrictor responses resulting from administration of exogenous norepinephrine. Thus, the composite data of Tables 1-2 indicate that doses of the trans-dl-racemate (and by implication, of the trans-4aR isomer, the active component of the racemate) which are hypotensive in intact SHR, result in selective inhibition of norepinephrine release from peripheral sympathetic nerve terminals.

TABLE 2

Selective antagonism of neurogenic vasoconstrictor responses produced by trans-dl-5-n-propyl-4,4a,5,6,7,8,8a,9-octahydro-1H—(and 2H)-pyrazolo[3,4-g]-quinoline.

| Trans-dl-racemate (mcg./kg., i.v.) | Increase in Diastolic Blood Pressure (mm. Hg.) Produced by Electrical Stimulation of the Sympathetic Outflow | | | |
|---|---|---|---|---|
| | 0.25 Hz | 1 Hz | 4 Hz | 8 Hz |
| none | 34 ± 3 | 72 ± 3 | 118 ± 8 | 129 ± 7 |
| 100 | 14 ± 2 | 47 ± 2 | 105 ± 8 | 115 ± 9 |
| 1000 | 10 ± 1 | 26 ± 4 | 65 + 8 | 89 ± 12 |

| Trans-dl-racemate (mcg./kg., i.v.) | Increase in Diastolic Blood Pressure (mm. Hg.) Produced by Exogenous Norepinephrine | | | |
|---|---|---|---|---|
| | 0.01 mcg./kg. | 0.1 mcg./kg. | 1 mcg./kg. | 10 mcg./kg. |
| none | 8 ± 1 | 27 ± 1 | 78 ± 3 | 140 ± 5 |
| 100 | 7 ± 1 | 29 ± 2 | 74 ± 1 | 128 ± 5 |
| 1000 | 10 ± 1 | 30 ± 2 | 80 ± 1 | 140 ± 4 |

The lack of alpha adrenergic receptor activity for trans-4aR-5-n-propyl-4,4a,5,6,7,8,8a,9-octahydro-1H(and 2H)pyrazolo[3,4-g]quinoline is illustrated by the following experiment in which vasoconstrictor activity (or lack thereof) can be demonstrated in pithed SHR as a rise in baseline blood pressure, vasoconstrictor activity resulting in a blood pressure rise.

The effects on blood pressure as a measure of the vasoconstrictor effects of trans-dl-5-n-propyl-4,4a,5,6,7,8,8a,9-octahydro-1H(and 2H)-pyrazolo[3,4-g]-quinoline and the trans-4aR stereoisomer were determined using norepinephrine as a control substance. Two other dopamine agonists, pergolide and lergotrile, were also included plus the 7-methylmercaptomethyl derivative of trans-dl-5-n-propyl-4,4a,5,6,7,8,8a,9-octahydro-1H(and 2H)pyrazolo[3,4-g]quinoline. Table 3 which follows gives the results of this comparison. In the table, column 1, gives the name of the test compound, column 2, the dose and column 3, the change in diastolic blood pressure. Four pithed SHR rats were used at each dose level for each drug.

TABLE 3

Relative blood pressure effects of trans-dl-5-n-propyl-4,4a,5,6,7,8,8a,9-octahydro-1H(and 2H)pyrazolo[3,4-g]quinoline, the trans-4aR stereoisomer and related compounds.

| Compound | IV Dose in mcg./kg. | Change in Diastolic Blood Pressure (mm. Hg.) |
|---|---|---|
| Trans-dl | 1 | +5 ± 1 |
| | 10 | +2 ± 3 |
| | 100 | +2 ± 4 |
| | 1000 | +7 ± 1 |
| Trans-4aR | 1 | −4 ± 1 |
| | 10 | −5 ± 1 |
| | 100 | −4 ± 1 |
| | 1000 | −3 ± 1 |
| Norepinephrine | .01 | +8 ± 1 |
| | .1 | +27 ± 1 |
| | 1 | +78 ± 3 |
| | 10 | +140 ± 5 |
| Pergolide | 1 | +4 |
| | 10 | +19 |
| | 100 | +62 |
| Lergotrile | 10 | +6 |
| | 100 | +6 |
| | 1000 | +18 |
| Trans-dl-5-n-propyl-7-methylmercaptomethyl-4,4a,5,6,7,8,8a,9-octahydro-1H— | 1 | +2 ± 2 |
| | 10 | +5 ± 1 |
| | 100 | +17 ± 1 |
| | 1000 | +49 ± 1 |

TABLE 3-continued

Relative blood pressure effects of trans-dl-5-n-propyl-4,4a,5,6,7,8,8a,9-octahydro-1H(and 2H)pyrazolo[3,4-g]quinoline, the trans-4aR stereoisomer and related compounds.

| Compound | IV Dose in mcg./kg. | Change in Diastolic Blood Pressure (mm. Hg.) |
|---|---|---|
| (and 2H)-pyrazolo-[3,4-g]quinoline | | |

From the above data, it would also be expected that the trans-4aR stereoisomer would not increase cardiac rate as does norepinephrine and this hypothesis has been affirmed by experiment.

It is apparent from the data presented in Tables 2-3 that trans-4aR-5-n-propyl-4,4a,5,6,7,8,8a,9-octahydro-1H(and 2H)pyrazolo[3,4-g]quinoline and the trans-dl racemate are neither an α-receptor agonists nor antagonists, that their hypotensive action is not caused by any α-receptor effect, but is probably attributable solely to their ability to block norepinephrine release from peripheral sympathetic nerve terminals that innervate arterial muscle fiber.

Trans-4aR-5-n-propyl-4,4a,5,6,7,8,8a,9-octahydro-1H-(and 2H)quinoline can be considered as related to the ergoline part structure (X) except that the pyrrole function is replaced by a pyrazole function (XIa and XIb).

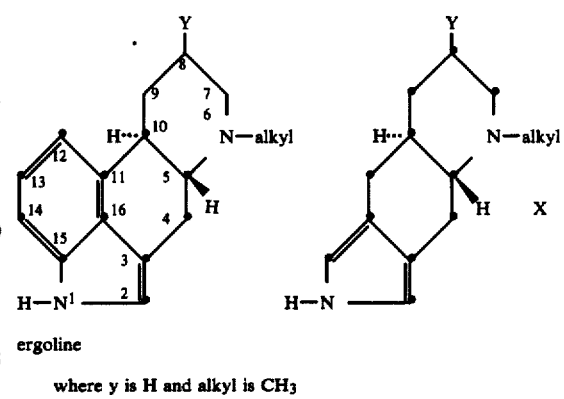

ergoline where y is H and alkyl is CH₃

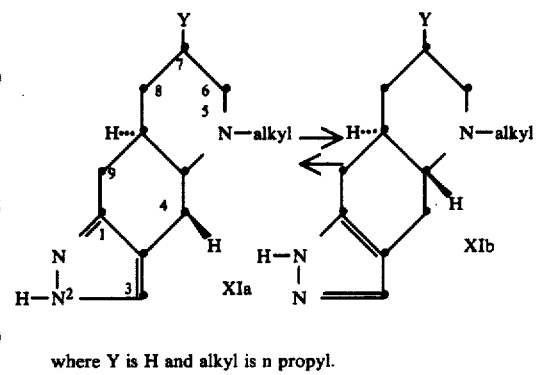

where Y is H and alkyl is n propyl.

Pergolide (see Table 2) is an ergoline where alkyl is n-propyl and Y is methylmercaptomethyl. Lergotrile (from Table 2) is an ergoline where alkyl is methyl, Y is CH₂CN and there is a chlorine at 2. The related compound trans-dl-5-n-propyl-7-methylmercaptomethyl-4,4a,5,6,7,8,8a,9-octahydro-1H(and 2H)pyrazolo[3,4- g]quinoline (XIa-b where alkyl is n-propyl and Y is methylmercaptomethyl), is disclosed in U.S. Pat. No. 4,198,415, and is a substituted derivative, in a sense, of the compound used in the process of this invention, the trans-4aR derivative, XIa-b where alkyl is also n-propyl but Y is H. From the data in Table 2, it can be seen that pergolide and trans-dl-5-n-propyl-7-methylmercaptomethyl-4,4a,5,6,7,8,8a,9-octahydro-1H(and 2H)pyrazolo[3,4-g]quinoline behave like norepinephrine in the pithed SHR. Thus, while these later compounds are dopamine agonists, they also act on α-receptors. Lergotrile, while it resembles the trans-4aR isomer useful in the process of this invention in that it does not act as a vascoconstrictor in pithed SHR, has undesirable central effects such as a potential for producing hallucinations in humans and is thus not a pure presynaptic dopamine agonist as is the trans-4aR isomer. The trans-4aR isomer is apparently unique as a presynaptic dopamine agonist. As a consequence, it is unique in its ability to lower an elevated blood pressure in mammals by blocking norepinephrine release from peripheral sympathetic nerve terminals that innervate arterial muscle fibers without other major pharmaceutical activity.

I claim:

1. The method of blocking norepinephrine release from peripheral sympathetic nerve terminals that innervate arterial muscle fibers in mammals which comprises administering to a mammal having an elevated blood pressure an effective dose of trans-4aR-5-n-propyl-4,4a,5,6,7,8,8a,9-octahydro-1H(and 2H)pyrazolo[3,4-g]quinoline or a pharmaceutically acceptable salt thereof, thereby blocking said norepinephrine release and reducing said elevated blood pressure.

2. A method according to claim 1 in which the D-(−)-S-tartrate salt is employed.

3. A method according to claim 1 in which the hydrochloride salt is employed.

4. A method according to claim 1 in which from 0.1 to 15 mg./kg./day of drug are administered orally.

* * * * *